United States Patent [19]

Eccli et al.

[11] Patent Number: 5,448,005
[45] Date of Patent: Sep. 5, 1995

[54] CRYSTALLIZATION OF PARAXLENE FROM HIGH PURITY PARAXYLENE FEEDS

[75] Inventors: William D. Eccli, Princeton Junction, N.J.; Alexander D. S. Fremuth, Langhorne, Pa.

[73] Assignee: Mobil Oil Corporation, Fairfax, Va.

[21] Appl. No.: 222,730

[22] Filed: Apr. 4, 1994

[51] Int. Cl.$^6$ ................................................ C07C 7/14
[52] U.S. Cl. ........................................ 585/812; 23/296
[58] Field of Search .......................................... 585/812

[56] References Cited

U.S. PATENT DOCUMENTS

| | | | |
|---|---|---|---|
| 3,177,265 | 4/1965 | Lammers | 585/812 |
| 3,662,013 | 5/1972 | Machell et al. | 260/674 A |
| 3,720,647 | 3/1973 | Gelbe et al. | 260/674 A |
| 4,097,543 | 6/1978 | Haag et al. | 260/672 T |
| 4,117,026 | 9/1978 | Haag et al. | 260/671 R |
| 4,851,604 | 7/1989 | Absil et al. | 585/475 |
| 5,173,461 | 12/1992 | Absil et al. | 502/62 |
| 5,243,117 | 9/1993 | Chang et al. | 585/467 |

FOREIGN PATENT DOCUMENTS

WO93/17788 9/1993 WIPO .

*Primary Examiner*—Anthony McFarlane
*Assistant Examiner*—Nhat D. Phan
*Attorney, Agent, or Firm*—Alexander J. McKillop; Dennis P. Santini; Lori F. Cuomo

[57] ABSTRACT

This invention is a crystallization process for p-xylene recovery. A single temperature crystallization production stage is used for producing p-xylene from a feed having an above equilibrium p-xylene concentration, such as from a toluene disproportionation process. Scavenger stages are also used to raise the p-xylene recovery rate.

24 Claims, 2 Drawing Sheets

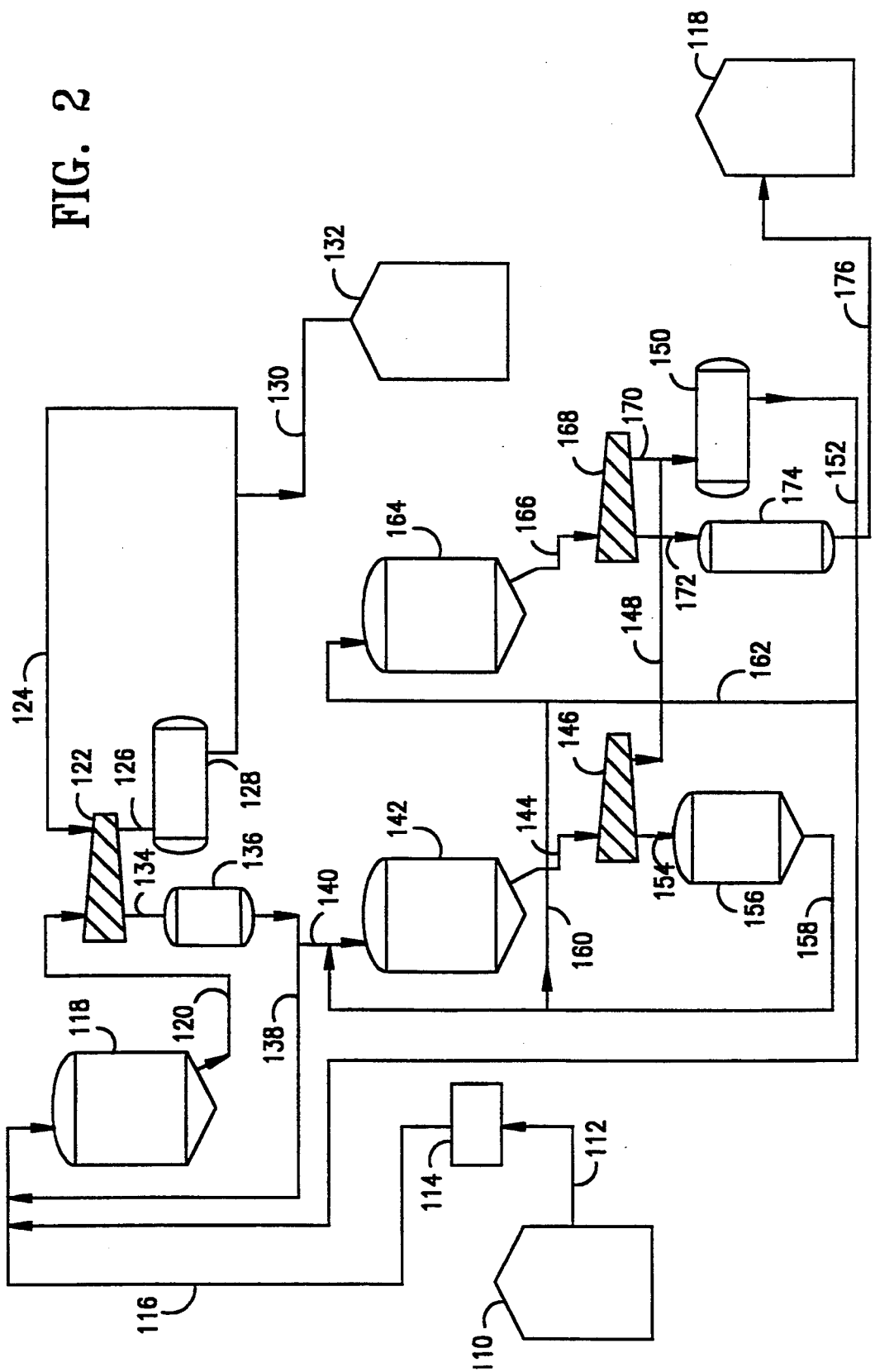

CRYSTALLIZATION OF PARAXLENE FROM HIGH PURITY PARAXYLENE FEEDS

CROSS-REFERENCE TO RELATED APPLICATIONS

This application is related by subject matter to Ser. No. 08 223,063, filed concurrently herewith.

FIELD OF THE INVENTION

The process of the present invention relates to a process for the crystallization of a feed having a high paraxylene concentration.

BACKGROUND

Crystallization methods can be used to separate paraxylene (p-xylene) from a $C_8$ aromatic starting material which contains ethylbenzene, as well as the three xylene isomers. Use is made of the fact that the melting point of the individual $C_8$ isomers have significant temperature differences. P-xylene has a freezing point of 13.3° C., metaxylene has a freezing point of −47.9° C. and orthoxylene has a freezing point of −25.2° C. However, conventional crystallization methods can be used to make p-xylene with a purity of over 99.5 wt. % only with great expense.

Crystallization processes to recover p-xylene from a mixture of $C_8$ aromatics requires cooling the equilibrium feed mixture from reformate or xylene isomerization processes. Because it's melting point is much higher than that of the other $C_8$ aromatics, p-xylene is readily separated in the crystallizer after refrigeration of the stream. In conventional p-xylene crystallization processes, the feed contains about 22 to about 23 wt. % p-xylene. In order to crystallize out most of the p-xylene from solution, the feed has to be cooled to as low as about −85° to −95° F. Conventional crystallization processes operate in the manner described in U.S. Pat. No. 3,662,013.

In conventional crystallization the maximum theoretical p-xylene recovery is fixed by the temperature of the coldest crystallizer in the crystallization unit. That temperature is limited by eutectic temperature, the temperature at which a second component, generally m-xylene, starts to crystallize and contaminates the p-xylene crystals. Given an equilibrium mixture of xylenes in the crystallizer feed, the coldest crystallizer is cooled to within 5°-10° F. of the eutectic temperature to maximize p-xylene recovery. Theoretically, the p-xylene recovery is limited to about 70% at the eutectic temperature. P-xylene recoveries of 60-65% are typical.

In a conventional two stage crystallizer. Equilibrium $C_8$ aromatic feed is cooled to about −30° F. to −40° F. and mixed with second stage filtrate and then crystallized in a number of crystallizers in series, each crystallizer cooling the feed further, the coldest of which runs typically at −80° F. to −90° F. The slurry solids and liquor, i.e. mother liquor, are separated by centrifuge. In the first stage, the solids become a wet cake with voids filled by the liquid containing only about 8-12 wt. % p-xylene. This low p-xylene liquid contaminates the crystals by 5-15%, depending on the drying efficiency of the centrifuge and prevents the p-xylene concentration from achieving the required 99.5+ wt. % purity. The remaining liquid is discharged as reject filtrate. This wet cake is either fully or partially melted and recrystallized or washed to remove the contaminants to achieve the required high p-xylene purity.

The second stage re-crystallizes the first stage product and filtrate p-xylene from the second stage recycle filtrate out of solution. The resulting slurry of crystals and mother liquor is centrifuged. The wet p-xylene crystals cake goes to the wash step, the remaining liquid is recycled filtrate. A controlled amount of the recycle filtrate is used to dilute the first stage product in order to control the slurry solids loading in the crystallizer. Typical centrifuges separate a slurry mixture containing no more than 35-45 wt. % solids. The second stage crystallizer operates at 0° to 40° F. and thus requires and processes a much smaller stream than the first stage and thus requires much less refrigeration.

The second stage cake voids are filled with liquid that is already rich in p-xylene, typically about 60-75 wt. %, and thus washing the crystals with product p-xylene can achieve a feed purity in the order of 99.5+ wt. % p-xylene.

A new approach to crystallization of p-xylene has now been found when processing a feed rich in p-xylene. It is an object of the present invention to provide an process for recovering paraxylene having a purity of at least 99.5 wt. % and preferably 99.8 wt. % from a feed rich in p-xylene.

SUMMARY OF THE INVENTION

It is believed that at a given a crystallizer temperature, as the p-xylene feed concentration increases, the p-xylene recovery increases. It is further believed that at a desired p-xylene recovery, as the feed concentration increases, the crystallizer temperature required to achieve this p-xylene recovery may be increased. Thus, at a fixed p-xylene feed concentration, as crystallizer temperature declines, p-xylene recovery increases.

With high enough p-xylene concentrations in the feed, the eutectic temperature is not a factor in the operation of the crystallizers of the present invention because cooling to the eutectic temperature is not required to get high p-xylene recovery rates. The use of scavenger stages further increases p-xylene recovery rates. Achievable p-xylene purity of at least 99.5 wt. % can be achieved in a single temperature crystallization production stage because of the high concentration of p-xylene in the feed and the high p-xylene concentration in the mother liquor.

The single temperature production stage crystallizer of the present invention employs a wash using p-xylene product. No other type of wash, such as toluene, is needed to produce 99.5 wt. % p-xylene purity. The p-xylene product of the present invention requires no further processing.

Therefore the invention includes a crystallization process to recover p-xylene from a feed rich in p-xylene which comprises:

contacting said feed rich in p-xylene in a single temperature crystallization production stage at a temperature in the range of from about 0° to about 50° F.;

withdrawing a slurry comprising p-xylene crystals from the production stage and passing said slurry from the production stage to a first separation means to form a cake and washing said cake with p-xylene;

passing said cake from said first separation means to a first melt drum to form p-xylene product and withdrawing said p-xylene product;

recycling a portion of reject filtrate from said first separation means to the production stage and recycling the remaining reject filtrate from the first separation means to a scavenger stage operated at a temperature lower than the temperature in the production stage, wherein the scavenger stage temperature is in the range of from about −20° to about 30° F.;

withdrawing a slurry comprising p-xylene crystals from said scavenger stage and passing said slurry from said scavenger stage to a second separation means to form a cake;

passing said cake from said second separation means to a second melt drum to form p-xylene crystals and recycling the p-xylene crystals to the production stage;

recycling a portion of reject filtrate from said second separation means to said scavenger stage and withdrawing the remaining reject filtrate from said second separation means as mother liquor product.

The invention further includes a crystallization process to recover p-xylene from a feed rich in p-xylene which comprises:

contacting said feed rich in p-xylene in a single temperature crystallization production stage at a temperature in the range of from about 0° to about 50° F.;

withdrawing a slurry comprising p-xylene crystals from the production stage and passing the slurry from the production stage to a first separation means to form a cake and washing said cake with p-xylene;

passing said cake from said first separation means to a first melt drum to form p-xylene product and withdrawing said p-xylene product;

recycling a portion of reject filtrate from said first separation means to the production stage and recycling the remaining reject filtrate from said first separation means to a first scavenger stage operated at a temperature lower than the temperature of the production stage, wherein the first scavenger stage temperature is in the range of from about 0° to about 30° F.;

withdrawing a slurry comprising p-xylene crystals from said first scavenger stage and passing said slurry from said first scavenger stage to a second separation means to form a cake;

passing said cake from said second separation means to a second melt drum to form p-xylene crystals and recycling said p-xylene crystals from said second melt drum to the production stage;

recycling a portion of reject filtrate from said second separation means to said first scavenger stage and passing the remaining reject filtrate from second separation means to a second scavenger stage operated at a temperature lower than the temperature of the first scavenger stage, wherein the second scavenger stage temperature is in the range of from about −20° to about 20° F.;

withdrawing a slurry comprising p-xylene crystals from second scavenger stage and passing said slurry from said second scavenger stage to a third separation means to form a cake;

passing said cake from said third separation means to said second melt drum to form p-xylene crystals and recycling said p-xylene crystals from said third separation means to said production stage; and recycling a portion of reject filtrate from said third separation means to said second scavenger stage and withdrawing the remaining reject filtrate as mother liquor product.

BRIEF DESCRIPTION OF THE DRAWING

FIG. 2 is a simplified schematic diagram showing the second embodiment of the present invention.

DETAILED DESCRIPTION OF THE INVENTION

Figure 1:
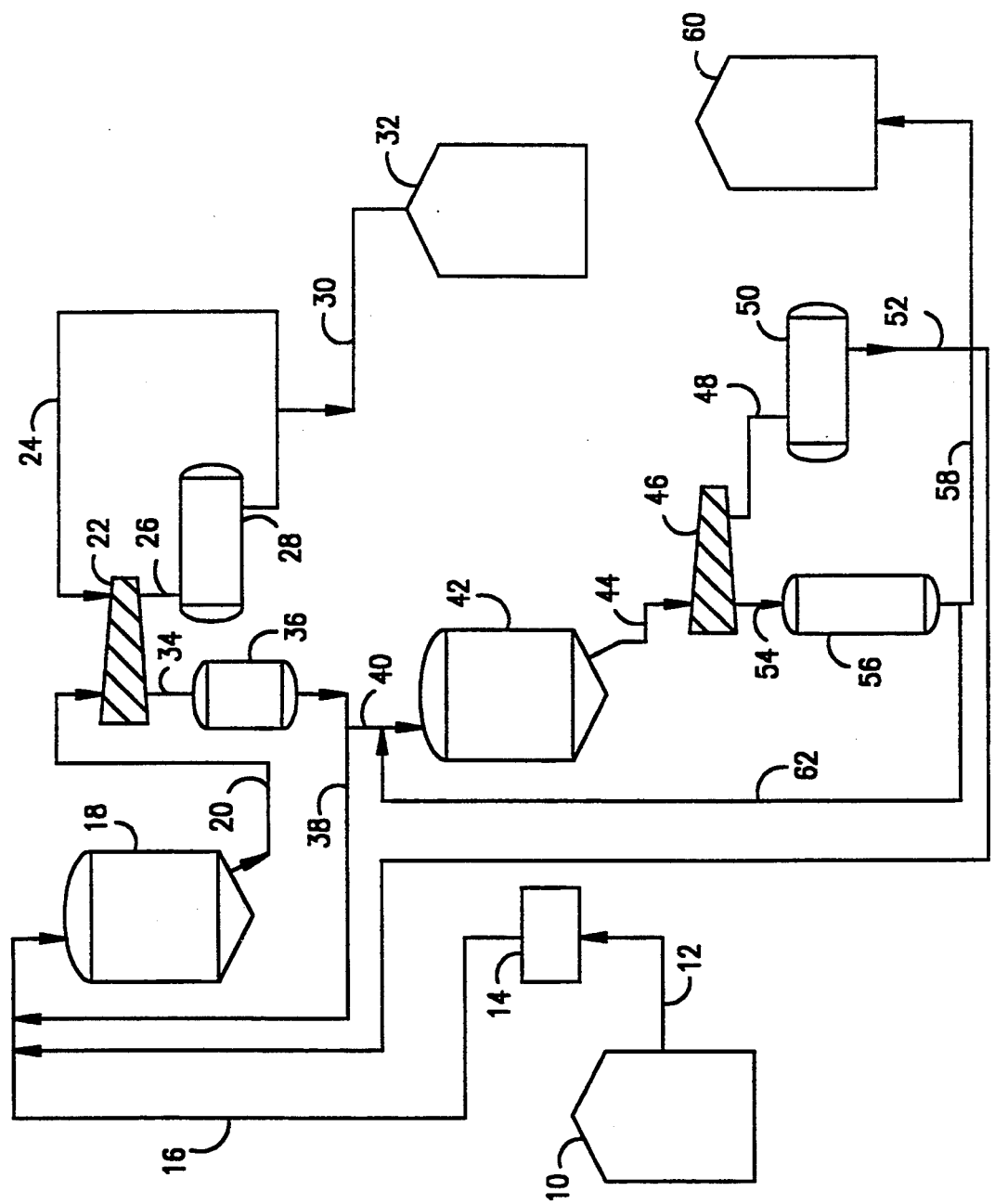
FIG. 1 is a simplified schematic diagram showing the first embodiment of the present invention.

The process of the present invention uses a high wt. % p-xylene feedstock, comprising at least about 70 wt. % p-xylene and preferably at least about 80 wt. % p-xylene.

Suitable feedstocks with high p-xylene concentration include products of processes which convert toluene to benzene and $C_8$ aromatics using a coke-selectivated or siliconselectivated catalyst, such as those described in U.S. Pat. Nos. 4,097,543 and 4,117,026, incorporated herein in their entirety by reference. Depending on the toluene conversion, about 80–85% of the $C_8$ aromatics are p-xylenes. Products of processes for the disproportionation of toluene to p-xylene using a silica-modified catalyst, such as those described in U.S. Pat. Nos. 4,851,604; 5,173,461; 5,243,117; and WO 93/17788 incorporated herein in their entirety by reference, may also be used. Different p-xylene concentration feeds may also be combined and may be used as the high p-xylene concentration feedstock of the present invention.

In the first embodiment, p-xylene rich feed enters a single temperature crystallization production stage from which high purity p-xylene product is produced. The crystallization product is then passed to a single scavenger stage to raise the p-xylene recovery rates but which does not produce p-xylene. The scavenger stage recycles the product produced from the melt drum to the feed of the single temperature crystallization production stage.

In a second embodiment, two scavenger stages are used in conjunction with the single temperature crystallization production stage to raise the p-xylene recovery rate but do not themselves produce p-xylene. This reduces the required refrigeration as compared to the use of a single scavenger stage.

The crystallization process of the present invention results in over about 80% recovery and preferably over 90% recovery to a purity above about 99.5 wt. % and preferably 99.8 wt. % p-xylenes.

The process includes a first crystallization production stage operated at a temperature in the range of from 0° F. to about 50° F. where high purity p-xylene is withdrawn. The production stage is the warmest stage in the process of the present invention. Recovery of p-xylene is enhanced by the use of one or two scavenger stages. In the first embodiment, one scavenger stage is employed. The scavenger stage is operated at a temperature lower than the crystallization production stage, generally in the range of about −20° F. to 30° F.

In the second embodiment, two scavenger stages are employed. The first scavenger stage is operated at a temperature between the first crystallization production stage temperature and the second scavenger stage temperature, generally at a temperature in the range of from about 0° F. to about 30° F. The second scavenger stage is operated at a temperature in the range of about −20° F. to about 20° F. and preferably at a temperature in the range of about −10° to about 10° F. The second recovery stage maximizes recovery of p-xylenes because it represents the coldest crystallization temperature.

The single temperature crystallization production stage and the scavenger stages are typically operated at pressures in the range of from about 20 psia to about 30 psia. The single temperature crystallization production stage and the scavenger stages are typically sized for a residence time in the range of from about 3 to about 8 hours and more typically in the range of from about 4 to about 8 hours for each stage.

The process of the present invention uses a single stage refrigeration system to cool the process to a minimum temperature of about −20° F. Propane or propylene can be used for the single refrigeration stage. The temperature of the coldest crystallizer may be lowered without having to use a two stage refrigeration system. At temperatures lower than 0° F., propylene is the preferred refrigerant.

The first embodiment of the present invention is illustrated in FIG. 1. A suitable p-xylene containing feed from feed tank 10 is passed through line 12 to heat exchanger 14 where it is initially cooled. The cooled feed is then passed through line 16 to a single temperature crystallization production stage 18. The single temperature production stage comprises one or more crystallizer vessels operated in parallel. In the single temperature production stage, the feed is cooled to a temperature at which p-xylene crystallizes without crystallization of other xylene isomers in the feed. Depending on the amounts of various components in the feed, this temperature will generally be in the range of from about 0° to about 50° F. and preferably from about 30 to about 50° F.

Slurry from the single temperature production stage is withdrawn through line 20 and passed to a centrifuge separation means 22. Alternatively, a filter or hydroclone may be used for separation. The centrifuged cake is washed with recycled p-xylene product. The washed cake is passed through line 26 and melted in melt drum 28. A portion of p-xylene product is recycled as wash liquor through line 24. The remaining p-xylene product is passed through line 30 to storage tank 32. The reject filtrate, i.e. mother liquor, from the single temperature production stage and reject p-xylene wash from centrifuge 22 are passed through line 34 to filtrate tank 36.

A portion of the reject filtrate is combined with the fresh feed to the single temperature production stage through line 38. The remaining reject filtrate passes through line 40 to a scavenger stage 42. The scavenger stage comprises one or more crystallizer vessels operated in parallel. Slurry from the scavenger stage is withdrawn through line 44 and passed to a centrifuge separation means 46. Alternatively, a filter or hydroclone may be used for separation. The centrifuged cake is passed through line 48 and melted in melt drum 50. The p-xylene crystals are recycled through line 52 as feed to the single temperature production stage. The reject filtrate, i.e. mother liquor from the scavenger stage, is passed through line 54 to filtrate tank 56. A portion of the reject filtrate passes through line 58 to storage tank 60. The reject filtrate product may be used as feed to a xylene isomerization unit. The remaining reject filtrate is combined with the fresh feed to the scavenger stage through line 62.

The second embodiment of the present invention using two scavenger stages is illustrated in FIG. 2. A suitable p-xylene containing feed from feed tank 110 is passed through line 112 to heat exchanger 114 where it is initially cooled. The cooled feed is then passed through line 116 to a single temperature production stage 118. The single temperature production stage comprises one or more crystallizer vessels operated in parallel. In the single temperature crystallization production stage, the feed is cooled to a temperature at which p-xylene crystallizes without crystallization of other xylene isomers in the feed. Depending on the amounts of various components in the feed, this temperature will generally be in the range of from about 0° F. to about 50° F. and preferably in the range of from about 30° F. to about 50° F.

Slurry from the single temperature production stage is withdrawn through line 120 and passed to a centrifuge separation means 122. Alternatively, a filter or hydroclone may be used for separation. The centrifuged cake is washed with recycled p-xylene product. The washed cake is passed through line 126 and melted in melt drum 128. A portion of p-xylene product is recycled as wash liquor through line 124. The remaining p-xylene product is passed through line 130 to storage tank 132. The reject filtrate, i.e. mother liquor, from the single temperature production stage and reject p-xylene wash are passed through line 134 to filtrate tank 136.

A portion of the reject filtrate is combined with the fresh feed to the single temperature production stage through line 138. The remaining reject filtrate passes through line 140 to a first scavenger stage 142. The first scavenger stage comprises one or more crystallizer vessels operated in parallel. Slurry from the scavenger stage is withdrawn through line 144 and passed to a centrifuge separation means 146. Alternatively, a filter or hydroclone may be used for separation. The centrifuged cake is passed through line 148 and melted in melt drum 150. The p-xylene crystals are recycled through line 152 as feed to the single temperature production stage.

The reject filtrate, i.e. mother liquor from the first scavenger stage, is passed through line 154 to filtrate tank 156. A portion of the reject filtrate passes through line 158 is combined with the fresh feed to the first scavenger stage. The remaining reject filtrate from the first scavenger stage passes through line 160 and is combined with reject filtrate from the second scavenger stage in line 162 as feed to the second scavenger stage 164. The second scavenger stage comprises one or more crystallizer vessels operated in parallel. Slurry from the second scavenger stage is withdrawn through line 166 and passed to a centrifuge separation means 168. Alternatively, a filter or hydroclone may be used for separation. The centrifuged cake is passed through line 170 and melted in melt drum 150. The p-xylene crystals are recycled through line 152 as feed to the single temperature production stage.

The reject filtrate, i.e. mother liquor from the second scavenger stage, is passed through line 172 to filtrate tank 174. A portion of the reject filtrate passes through line 162 as feed to the second scavenger stage. The remaining reject filtrate passes through line 176 to storage tank 178. The reject filtrate product may be used as feed to a xylene isomerization unit.

The following example illustrates the process of the present invention.

EXAMPLE 1

This example illustrates the operation of the process flow scheme of FIG. 2 in carrying out the crystallization of p-xylene to produce 600 million lb./year. A p-xylene containing feed having a p-xylene concentration of about 93.2% is contacted in a single temperature crystallization production stage operated at a temperature of about 37°–40° F. The p-xylene product is withdrawn from the single temperature crystallization production stage after the centrifuged cake is washed with recycled p-xylene product to achieve a p-xylene product purity of 99.8–99.9%. Using a first scavenger stage operated at 25° F. and a second scavenger stage operated at 0° F. maximizes recovery of p-xylene to achieve a 94% p-xylene recovery.

Changes and modifications in the specifically described embodiments can be carried out without departing from the scope of the invention which is intended to be limited only by the scope of the appended claims.

We claim:

1. A crystallization process to recover p-xylene from a feed rich in p-xylene which comprises:

contacting said feed rich in p-xylene in a single temperature crystallization production stage at a temperature in the range of from about 0° to about 50° F.;

withdrawing a slurry comprising p-xylene crystals from the production stage and passing said slurry from the production stage to a first separation means to form a cake and washing said cake with p-xylene;

passing said cake from said first separation means to a first melt drum to form p-xylene product and withdrawing said p-xylene product;

recycling a portion of reject filtrate from said first separation means to the production stage and passing the remaining reject filtrate from the first separation means to a scavenger stage operated at a temperature lower than the temperature in the production stage, wherein the scavenger stage temperature is in the range of from about −20° to about 30° F.;

withdrawing a slurry comprising p-xylene crystals from said scavenger stage and passing said slurry from said scavenger stage to a second separation means to form a cake;

passing said cake from said second separation means to a second melt drum to form p-xylene crystals and recycling the p-xylene crystals to the production stage;

recycling a portion of reject filtrate from said second separation means to said scavenger stage and withdrawing the remaining reject filtrate from said second separation means as mother liquor product.

2. The process according to claim 1 wherein said single temperature stage crystallization production stage is operated at a temperature in the range of from about 30° F. to about 50° F.

3. The process according to claim 1 wherein said feed rich in p-xylene comprises at least about 70 wt. % p-xylene.

4. The process according to claim 1 wherein said feed rich in p-xylene comprises at least about 80 wt. % p-xylene.

5. The process according to claim 1 wherein the withdrawn p-xylene product has at least about a 99.5 wt. % p-xylene product purity.

6. The process according to claim 1 wherein the withdrawn p-xylene product has at least about a 99.8 wt. % p-xylene product purity.

7. The process according to claim 1 wherein the cake formed in said first separation means is washed with recycled p-xylene product from said first melt drum.

8. The process according to claim 1 wherein said first separation means, second separation means and third separation means comprise a centrifuge.

9. The process according to claim 1 wherein said feed is a product of toluene disproportionation using a silica-modified catalyst.

10. The process according to claim 1 wherein said feed is a product of a process to convert toluene to benzene and C8 aromatics using a coke-selectivated or silicon-selectivated catalyst.

11. The process according to claim 1 wherein over 80% of the p-xylene in said feed is recovered.

12. The process according to claim 1 wherein over 90% of the p-xylene in said feed is recovered.

13. A crystallization process to recover p-xylene from a feed rich in p-xylene which comprises:

contacting said feed rich in p-xylene in a single temperature crystallization production stage at a temperature in the range of from about 0° to about 50° F.;

withdrawing a slurry comprising p-xylene crystals from the production stage and passing the slurry from the production stage to a first separation means to form a cake and washing said cake with p-xylene;

passing said cake from said first separation means to a first melt drum to form p-xylene product and withdrawing said p-xylene product;

recycling a portion of reject filtrate from said first separation means to the production stage and passing the remaining reject filtrate from said first separation means to a first scavenger stage operated at a temperature lower than the temperature of the production stage, wherein the first scavenger stage temperature is in the range of from about 0° to about 30° F.;

withdrawing a slurry comprising p-xylene crystals from said first scavenger stage and passing said slurry from said first scavenger stage to a second separation means to form a cake;

passing said cake from said second separation means to a second melt drum to form p-xylene crystals and recycling said p-xylene crystals from said second melt drum to the production stage;

recycling a portion of reject filtrate from said second separation means to said first scavenger stage and passing the remaining reject filtrate from second separation means to a second scavenger stage operated at a temperature lower than the temperature of the first scavenger stage, wherein the second scavenger stage temperature is in the range of from about −20 to about 20° F.;

withdrawing a slurry comprising p-xylene crystals from second scavenger stage and passing said slurry from said second scavenger stage to a third separation means to form a cake;

passing said cake from said third separation means to said second melt drum to form p-xylene crystals and recycling said p-xylene crystals from said third separation means to said production stage; and recycling a portion of reject filtrate from said third separation means to said second scavenger stage and withdrawing the remaining reject filtrate as mother liquor product.

14. The process according to claim 13 wherein said single temperature stage crystallization production stage is operated at a temperature in the range of from about 30° F. to about 50° F.

15. The process according to claim 13 wherein said feed rich in p-xylene comprises at least about 70 wt. % p-xylene.

16. The process according to claim 13 wherein said feed rich in p-xylene comprises at least about 80 wt. % p-xylene.

17. The process according to claim 13 wherein the withdrawn p-xylene product has at least about a 99.5 wt. % p-xylene product purity.

18. The process according to claim 13 wherein the withdrawn p-xylene product has at least about a 99.8 wt. % p-xylene product purity.

19. The process according to claim 13 wherein the cake formed in said first separation means is washed with recycled p-xylene product from said first melt drum.

20. The process according to claim 13 wherein said first separation means, second separation means and third separation means comprise a centrifuge.

21. The process according to claim 13 wherein said feed is a product of toluene disproportionation using a silica-modified catalyst.

22. The process according to claim 13 wherein said feed is a product of a process to convert toluene to benzene and $C_8$ aromatics using a coke-selectivated or silicon-selectivated catalyst.

23. The process according to claim 13 wherein over 80% of the p-xylene in said feed is recovered.

24. The process according to claim 13 wherein over 90% of the p-xylene in said feed is recovered.

* * * * *